United States Patent [19]
Neal

[11] Patent Number: 6,103,765
[45] Date of Patent: Aug. 15, 2000

[54] METHODS FOR TREATING MALE ERECTILE DYSFUNCTION

[75] Inventor: Gary W. Neal, Knoxville, Tenn.

[73] Assignee: Androsolutions, Inc., Knoxville, Tenn.

[21] Appl. No.: 08/890,445

[22] Filed: Jul. 9, 1997

[51] Int. Cl.[7] .................. A61K 31/19; A61K 31/557
[52] U.S. Cl. .................. 514/573; 424/195.1; 514/33; 514/574; 514/691
[58] Field of Search .................. 514/573, 33, 574, 514/691; 424/465, 195.1

[56] References Cited

U.S. PATENT DOCUMENTS

| | | |
|---|---|---|
| 3,070,623 | 12/1962 | Gottfried et al. . |
| 3,161,654 | 12/1964 | Shen . |
| 3,647,858 | 3/1972 | Hinkley et al. . |
| 3,654,349 | 4/1972 | Shen et al. . |
| 3,657,327 | 4/1972 | Morozowich . |
| 3,843,681 | 10/1974 | Demerson et al. . |
| 3,965,143 | 6/1976 | Collins et al. . |
| 4,085,135 | 4/1978 | Kyogoku et al. . |
| 4,127,118 | 11/1978 | Latorre . |
| 4,178,457 | 12/1979 | Van Horn et al. . |
| 4,198,406 | 4/1980 | Hardy et al. . |
| 4,215,128 | 7/1980 | Howarth . |
| 4,311,707 | 1/1982 | Birnbaum et al. . |
| 4,503,040 | 3/1985 | Barth . |
| 4,539,333 | 9/1985 | Moncada . |
| 4,725,439 | 2/1988 | Campbell et al. . |
| 4,766,889 | 8/1988 | Trick et al. . |
| 4,801,587 | 1/1989 | Voss et al. . |
| 4,829,991 | 5/1989 | Boeck . |
| 4,857,059 | 8/1989 | Rey et al. . |
| 4,867,982 | 9/1989 | Campbell et al. . |
| 5,049,384 | 9/1991 | Kim . |
| 5,059,603 | 10/1991 | Rubin . |
| 5,147,855 | 9/1992 | Gozes et al. . |
| 5,190,967 | 3/1993 | Riley . |
| 5,242,391 | 9/1993 | Place et al. . |
| 5,256,652 | 10/1993 | El-Rashidy . |
| 5,270,323 | 12/1993 | Milne, Jr. et al. . |
| 5,474,535 | 12/1995 | Place et al. . |
| 5,482,039 | 1/1996 | Place . |
| 5,571,118 | 11/1996 | Boutos . |
| 5,574,068 | 11/1996 | Stamler et al. . |
| 5,583,144 | 12/1996 | Kral . |
| 5,612,314 | 3/1997 | Stamler et al. . |
| 5,631,284 | 5/1997 | Legzdins et al. . |
| 5,646,181 | 7/1997 | Fung et al. . |
| 5,648,393 | 7/1997 | Stamler et al. . |
| 5,681,850 | 10/1997 | Frolich et al. . |
| 5,708,031 | 1/1998 | Scott . |
| 5,718,917 | 2/1998 | See . |
| 5,731,339 | 3/1998 | Lowrey . |
| 5,769,088 | 6/1998 | Place . |
| 5,770,606 | 6/1998 | El-Rashidy et al. . |
| 5,773,020 | 6/1998 | Place et al. . |

FOREIGN PATENT DOCUMENTS

| | | |
|---|---|---|
| 0 357 581 | 3/1990 | European Pat. Off. . |
| PCT/US98/ 13439 | 7/1998 | WIPO . |

OTHER PUBLICATIONS

Robert J. Krane, et al, *N. Eng. J. Med*, vol. 321, No. 24, pp. 1648–1659 (1989).
Virag, et al, *Angiology*, vol. 35, pp. 79–87, 1984.
M. Ishii et al, *J. of Urol.*, vol. 141, pp. 323–325 (1989).
Schmidt, *JAMA*, vol. 259, No. 21, pp. 3176 (1988).
Bergstrom et al, *J. Biol. Chem.*, vol. 238, pp. 3555–3564 (1963).
Corey et al, *J. Am. Chem. Soc.*, vol. 91, p. 535 (1969).
Corey et al, *J. Am. Chem. Soc.*, vol. 92, p. 2586 (1970).
Sih et al, *J. Am. Chem. Soc.*, vol. 94, p. 3643 (1972).
Sih et al, *J. Am. Chem. Soc.*, vol. 95, p. 1676 (1973).
Schaaf et al, *J. Org. Chem.*, vol. 37, p. 2921 (1974).
Slates et al, *Tetrahedron*, vol. 30, pp. 819–830 (1974).
Corey et al, *J. Am. Chem. Soc.*, vol. 92, p. 397 (1970).
Heather et al, *Tetrahedron Letters*, pp. 2313–2316 (1973).
Mak et al, *Biochimica et Biophysica Acta*, vol. 1035, pp. 190–196 (1990).
Ensor et al, *J. Lipid Mediators Cell Signalling*, vol. 12, pp. 313–319 (1995).
Chang et al, *Biochem. Biophys. Res. Commun.*, vol. 99, pp. 745–751 (1981).
Jarabak et al, *Prostaglandins*, vol. 18, pp. 241–246 (1979).
Lin et al, *Biochem. Biophys. Res. Commun.*, vol. 81, pp. 1227–1234 (1978).
Hosoda et al, *J. Org. Chem.*, vol. 38, p. 4209 (1973).
Herin Padam–Nathan et al, *New England Journal of Medicine*, vol. 336, pp. 1–7 (Jan. 2, 1997).
Rosen et al, *Archives of Sexual Behavior*, vol. 22(6), pp. 521–543 (1993).
G.M. Craig, *PMJ*, vol. 51, pp. 74–84 (1975).
J. LoPiccolo et al, *J. of Counseling and Clinical Psychology*, vol. 54(2), pp. 158–167 (1986).
Gringanz, *Introduction to Medicinal Chemistry*, Wiley–VCH, Inc., New York, pp. 155–161 and 640–643 (1997).
Yamamura et al, *J. Chromatogr.*, vol. 331, pp. 383–388 (1985).
Uekama et al, *J. Pharm. Sci.*, vol. 73, pp. 382–384 (1984).
Yamamura et al, *J. Chromatogr.*, vol. 303, pp. 165–172 (1984).
Merck Index, 10th Edition, citation 4368, 1983, p. 647, Budavari et al.
Berry et al, *Biochemical Pharmacology*, vol. 32, pp. 2863–2871 (1983).
H. Willimann et al, *J. of Pharmaceutical Sciences*, vol. 81, pp. 871–874 (1992).
Goldstein et al, Abstract #919, *The Journal of Urology*, V. 159(5), p. 240 (May 1998).

(List continued on next page.)

*Primary Examiner*—M Moezie
*Attorney, Agent, or Firm*—Oblon, Spivak, McClelland, Maier & Neustadt, P.C.

[57] ABSTRACT

Administration of a pharmaceutical composition comprising:
(a) a vasodilator; and
(b) a 15-hydroxyprostaglandindehydrogenase inhibitor is effective for the treatment of male erectile dysfunction.

19 Claims, 1 Drawing Sheet

OTHER PUBLICATIONS

M. Muramatsu, *Biochemical Pharmacology*, vol. 33, pp. 2629–2633 (1984).
C.L. Tai et al, *Biochem. J.*, vol. 267, pp. 75–78 (1990).
H. Hedlund et al, *J. Urol.*, vol. 134, pp. 1245–1250 (1985).
F. Pichaud et al, *Blood*, vol. 89, pp. 2105–2112 (1997).
M. Waldhauser et al, *J. Urology*, vol. 140, pp. 525–527 (1988).
M. E. Baker, *Steroids*, vol. 59, pp. 136–141 (1994).
H. Porst, *J. Urology*, vol. 155, pp. 802–815 (1996).
K. Takeuchi et al, *Gen. Pharmac.*, vol. 30, pp. 739–744 (1988).
A.C. Roy et al, *Brit. J. Urology*, vol. 64, pp. 180–182 (1989).
E. Anggard et al, *Agents and Actions*, vol. 6/4, pp. 498–504 (1976).
G. Galea et al, *J. Urology*, vol. 159, p. 236, Abstract No. 903 (1998).
S. Sakuma et al, *Prostaglandins*, vol. 40, pp. 507–514 (1990).
J. Jarabak, *Prostaglandins*, vol. 35, pp. 403–411 (1988).
Y. Iijima et al, *Biochem. and Biophys. Res. Comm.*, vol. 80, pp. 484–489 (1978).
D. T.–Y. Kung–Chao et al, *Biochemica et Biophysica Acta*, vol. 614, pp. 1–13 (1980).
C. G. Stief et al, *J. Urology*, vol. 159, pp. 1390–1393 (1998).
Peskar et al, *J. Pharm. Pharmacol.*, vol. 28, pp. 146–148 (1976).
Virag et al, *J. Urology*, vol. 137, p. 1010 (1987).
Linet et al, *New England Journal of Medicine*, vol. 334, pp. 873–877 (Apr. 4, 1996).
Wolfson et al, *Urology*, vol. 42, pp. 73–75 (1993).
*Diagnostic and Statistical Manual IV*, "Sexual and Gender Identity Disorder", American Psychiatric Association, Washington, D.C., pp. 493–539 and 735–751 (1994).
Nathan, *J. of Sex and Marital Therapy*, vol. 12, No. 4, pp. 267–281 (1986).
Osborn et al, *British Medical Journal*, vol. 296, pp. 959–962 (1988).
Frank et al, *New England Journal of Medicine*, vol. 299, pp. 111–115 (1978).
Basar et al, *International Urology and Nephrology*, vol. 29, pp. 667–671 (1997).
*Proceeding of the American Urological Association*, vol. 153, Apr. 1995 Supplement, Abstracts 976 and 977.
Goodman Gilman et al., "The Parmacological Basis of Therapeutics" (6th Ed.), New York, pp. 668–678. 1980.
Cawello et al, *Journal of Urology*, vol. 158, pp. 1403–1407 (1997).
van Ahlen et al., *Journal of Urology*, vol. 151, 1227–1230 (1994).
Chen et al, *Journal of Clinical Ultrasound*, vol. 20, pp. 247–253 (1992).
*Harrison's Principles of Internal Medicine*, Thirteenth Ed., K. J. Isselbacher et al, Eds., McGraw–Hill, Inc., New York. p. 2492 (1994).
Foldvari et al, *European Journal of Drug Metabolism and Pharmacokinetics*, vol. 22 (2), pp. 111–120 (1997).
Alam et al, *Endocrinology*, vol. 98 (4), pp. 859–863 (1976).
Franchi et al, *Prostaglandins*, vol. 29 (6), pp. 953–960 (1985).
Stackl et al, *Journal of Urology*, vol. 140, pp. 66–68 (1998).
Migeon et al, *The Johns Hopkins Medical Journal*, vol. 123, pp. 128–133 (1968).
Futterweit et al, *Metabolism*, vol. 33 (10), pp. 936–942 (1984).
Notification of Transmittal of the International Search Report or the Declaration issued on Nov. 17, 1998, in corresponding PCT/US98/13439.
U.S. application No. 08/954,122, filed Oct. 20, 1997, Pending.
U.S. application No. 60/068294, filed Dec. 19, 1997, Pending.
U.S. application No. 09/215,295, filed Dec. 18, 1998, Pending.
Änggård et al, *Ark. Kem.*, vol. 25, pp. 293–300 (1966).
Garde et al, *Maturitas*, vol. 2, pp. 225–240 (1980).
Handelsman, "Diagnosis and Treatment of Impotence" in AHCPR Health Technology Assessment Reports, No. 2, pp. 1–24 (1990).
Bergstrom et al, *Acta Chem. Scand.*, vol. 16, p. 501–504 (1962).
Macdonald, *Biochem. Biophys. Acta.*, vol. 1061, pp. 297–303 (1991).
Althof et al, *J. Sex & Marital Therapy*, vol. 13, pp. 155–167 (1987).
Benkert et al, *Psychopharmacologia*, vol. 23, pp. 91–95 (1972).
Utiger, *N. England J. Med.*, vol. 338, pp. 1458–1459 (1998).
Siegel–Itzkovich, *BMJ*, vol. 316, p. 1625 (1998).
Bodner et al, *J. Urol.*, vol. 138, pp. 310–311 (1987).
Lal et al, *Prog. Neuro–Pschopharmacol. & Biol. Psychiat.*, vol. 11, pp. 235–242 (1987).
Goldstein et al, *N. England J. Med.*, vol. 338, pp. 1397–1404 (1998).
Hyyppä et al, in *Sexual Behavior Pharmacology and Biochenistry*, M. Sandler et al, Eds., Plenum Press, New York, pp. 315–327 (1975).
Virag et al, *Angiol.*, vol. 35, pp. 79–87 (1984).
Virag et al *J. of Urol.*, vol. 137, p. 1010 (1987).
Chang, *Advances in Prostaglandin, Thromboxane, and Leukotriene Research*, vol. 19, pp. 225–228 (1989).

METHODS FOR TREATING MALE ERECTILE DYSFUNCTION

BACKGROUND OF THE INVENTION

1. Field of the Invention

The present invention relates to methods of treating male erectile dysfunction. The present invention further relates to pharmaceutical compositions useful for treating male erectile dysfunction.

2. Discussion of the Background

Impotence, or lack of a man's ability to have sexual intercourse, is often the subject of jokes. However, millions of men suffer from this condition. Impotence is generally characterized by an inability to maintain a penile erection, and is often referred to as erectile dysfunction. Erectile dysfunction affects men, regardless of age, place of birth, or prior sexual experience.

In the context of the present invention, the term "erectile dysfunction" refers to certain disorders of the cavernous tissue of the penis and the associated fascia which produce impotence, the inability to attain a sexually functional erection. Impotence is estimated to affect about 10 million men in the United States alone. Impotence results from disruption of any of numerous physiological or psychological factors which cause the blood flow to and from the penis to remain in balance thereby preventing retention of sufficient blood to cause rigid dilation of the corpus cavernosa and spongiosa. In the context of the present invention, the term "impotence" is used in its broadest sense as the inability to attain a sexually functional erection when desired.

Treatments for impotence include psychosexual therapy, hormonal therapy, administration of vasodilators such as nitroglycerin and α-adrenergic blocking agents (hereafter "α-blockers"), vascular surgery, implanted penile prostheses, vacuum devices and external aids such as penile splints to support the penis or penile constricting rings to alter the flow of blood through the penis, (see Robert J. Krause, et al., *N. Eng. J. Med.* vol. 321, No 24, Dec. 14, 1989). Many patients treat their impotence by self injection of vasoactive drugs directly into the corpora cavernosa (see: Forward *1ˢᵗ Symposium International Sur L'Erection Pharmacologique*, Nov. 17–19, 1989, Paris, p. 2; Virag, et al., *Angiology*, vol. 35, pp. 79–87, (1984); and U.S. Pat. Nos. 4,127,118, 4,766,889, and 4,857,059, which are incorporated herein by reference). The drugs most commonly used include α-blockers, such as phenoxybenzamine and phentolamine; smooth muscle relaxants such as papaverine; prostaglandins having a vasoactive function such as prostaglandin $E_1$ and combinations of such drugs having different receptor effects to enhance therapy. Intracavernous injection doses of papaverine are typically in the range of about 7.5 to 160 mg, while doses of phentolamine are in the range of about 0.1 to 10 mg and doses of prostaglandin $E_1$ are in the range of about 2.5 to 50 micrograms (see for example, Kurkle, et al., *Urol. Clin. of America*, vol. 15, No. 4, pp. 625–629 (1988) and N. Ishii et al., *J. of Urol.*, vol. 141, pp. 323–325 (1989). Vasoactive intestinal peptides have also been reported as producing erection upon intracavernous injection at doses of 10–100 µg (see H. Handelsman, *Diagnosis and Treatment of Impotence*, U.S. Dept. of Health Services, Agency for Health Care Policy and Research, April 1990).

However, patients often find the injections of vasoactive drugs psychologically disturbing, painful, traumatic, or inconvenient as evidenced by a high discontinuance rate (see S. Althouf, et al., *Journal of Sex and Marital Therapy*, vol. 15, No. 2, pp. 121–129 (1989). In addition, adverse side effects including priapism, corporeal nodules and diffuse fibrosis, drug tolerance, bruising and hematomas, swelling and ulceration of the penile skin at the injection site have also been reported.

U.S. Pat. No. 4,801,587 and EPA 0357581 disclose the administration of vasodilators via the male urethra to produce erections. The transurethral administration of testosterone has also been reported (see S. M. Milco, *Bulletins et Memoirs de la Societa Roumaine D'Endocrinologie*, Vol. 5, pp. 434–437 (1989)). It has also been suggested that cocaine administered transurethrally could contribute to an erection (*JAMA*, vol. 259, No. 21, page 3176 (1988)). A nitroglycerin coated, erection inducing condom is disclosed in U.S. Pat. No. 4,829,991.

However, to date there is no completely effective treatment for male erectile dysfunction. Thus, there remains a need for a method of treating male erectile dysfunction. There also remains a need for compositions which are effective for treating male erectile dysfunction. In particular, there remains a need for methods and compositions for treating impotence which are characterized by a reduced tendency to cause pain, priapism, corporeal nodules, diffuse fibrosis, and scarring.

SUMMARY OF THE INVENTION

Accordingly, it is one object of the present invention to provide novel methods for treating male erectile dysfunction.

It is another object of the present invention to provide methods for treating male erectile dysfinction involving topical administration of a pharmaceutical composition.

It is another object of the present invention to provide methods for treating male erectile dysfunction which exhibit a reduced tendency to cause pain or a burning sensation.

It is another object of the present invention to provide methods for treating male erectile dysfunction which exhibit a reduced tendency to cause priapism.

It is another object of the present invention to provide methods for treating male erectile dysfunction which exhibit a reduced tendency to cause corporeal nodules.

It is another object of the present invention to provide methods for treating male erectile dysfunction which exhibit a reduced tendency to cause diffuse fibrosis.

It is another object of the present invention to provide methods for treating male erectile dysfunction which exhibit a reduced tendency to cause scarring of the corpora spongiosum and cavernosa.

It is another object of the present invention to provide novel pharmaceutical compositions which are useful for treating male erectile dysfunction.

It is another object of the present invention to provide pharmaceutical compositions for treating male erectile dysfunction which exhibit a reduced tendency to cause pain or a burning sensation.

It is another object of the present invention to provide pharmaceutical compositions for treating male erectile dysfunction which exhibit a reduced tendency to cause priapism.

It is another object of the present invention to provide pharmaceutical compositions for treating male erectile dysfunction which exhibit a reduced tendency to cause corporeal nodules.

It is another object of the present invention to provide pharmaceutical compositions for treating male erectile dysfunction which are effective when applied topically.

It is another object of the present invention to provide pharmaceutical compositions for treating male erectile dysfunction which exhibit a reduced tendency to cause diffuse fibrosis.

It is another object of the present invention to provide pharmaceutical compositions for treating male erectile dysfunction which exhibit a reduced tendency to cause scarring of the corpora spongiosum and cavernosa.

These and other objects, which will become clear in the course of the following detailed description, have been achieved by the inventor's discovery that pharmaceutical compositions comprising: (a) a vasodilator; and (b) a 15-hydroxyprostaglandindehydrogenase inhibitor, are particularly effective for the treatment of male erectile dysfunction even at low doses.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein.

DETAILED DESCRIPTION OF THE PREFERRED EMBODIMENTS

Figure 1:
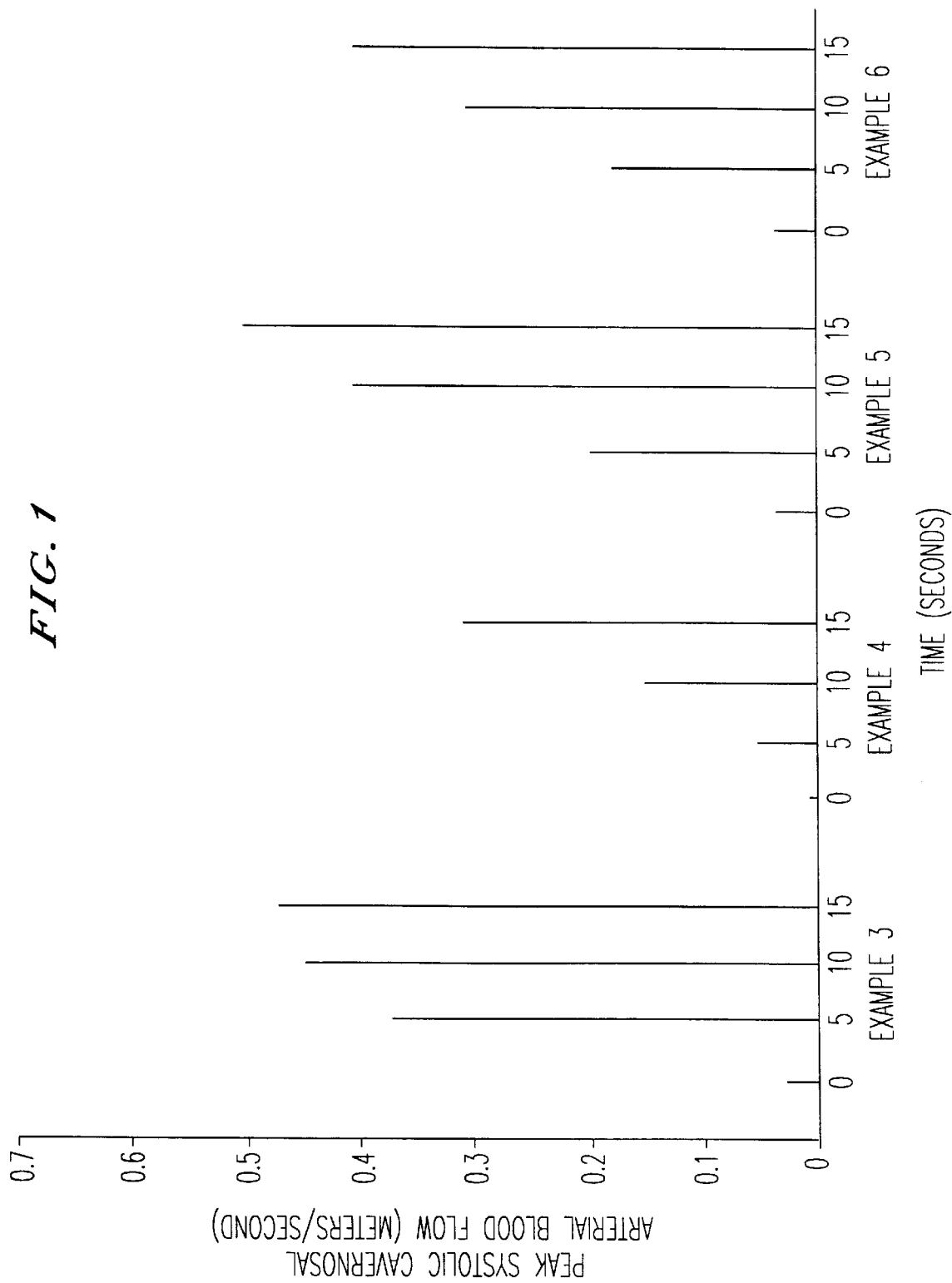
FIG. 1 graphically illustrates the peak systolic blood flow in the cavernosal artery (meters/second) as a function of time (minutes) after administration of some compositions according to the present invention.

Thus, in a first embodiment, the present invention provides novel pharmaceutical compositions which are useful for treating male erectile dysfunction. The present pharmaceutical compositions are characterized as comprising (a) a vasodilator; and (b) a 15-hydroxyprostaglandindehydrogenase inhibitor.

The vasodilator may be any physiologically acceptable vasodilator. Examples of suitable vasodilators include: (a) alpha-blockers, such as phentolamine, prazosin, doxazosin, phenoxybenzanmine, dibenzamine, terazosin, tolazoline, and trimazosin; (b) vasodilating adrenoreceptor agents, such as carvedilol, labetolol, yohimbine, and terbutaline; (c) nonspecific vasodilating, substances, such as papaverine, nitrates, and nitroso compounds (e.g., nitroglycerin); and (d) other agents, such as vasoactive intestinal peptide.

Preferably, the vasodilator is a prostaglandin, such as misoprostol, enprostil, prostaglandin $I_2$, prostaglandin $F_2$, prostaglandin $E_1$, or prostaglandin $E_2$. Good results have been achieved by using either prostaglandin $E_1$ or prostaglandin $E_2$.

Prostaglandin $E_1$ is also known as alprostadil or $PGE_1$. The formal chemical name of prostaglandin $E_1$ is 3-hydroxy-2-(3-hydroxy-1-octenyl)-5-oxocyclopetaneheptanoic acid, and the structure of prostaglandin $E_1$ is

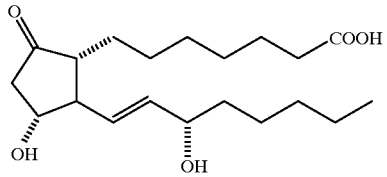

Prostaglandin $E_1$ may be isolated from sheep seminal vesicle tissue as described in Bergstrom et al., *Acta. Chem. Scand.,* vol. 16, p. 501 (1962) and *J. Biol. Chem.,* vol. 238, p. 3555 (1963). The synthesis of prostaglandin $E_1$ may be carried out as described in Corey et al., *J. Am. Chem. Soc.,* vol. 91, p. 535 (1969); Corey et al., *J. Am. Chem. Soc.,* vol. 92, p. 2586 (1970); Sih et al., *J. Am. Chem. Soc .,* vol. 94, p. 3643 (1972); Sih et al., *J. Am. Chem. Soc.,* vol. 95, p. 1676 (1973); Schaaf et al., *J. Org. Chem.,* vol. 37, p. 2921 (1974); and Slates et al., *Tetrahedron,* vol. 30, p. 819 (1974).

Prostaglandin $E_2$ is also known as dinoprostone or $PGE_2$. The formal chemical name of prostaglandin $E_2$ is 7-[3-hydroxy-2-(3-hydroxy-1-octenyl)-5-oxocyclopentyl]-5-heptenoic acid, and the structure of prostaglandin $E_2$ is:

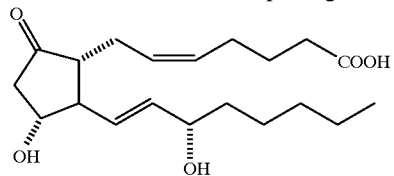

Prostaglandin $E_2$ may be isolated from sheep seminal vesicle tissue as described in Bergstrom et al., *Acta. Chem. Scand.,* vol. 16, p. 501 (1962). Prostaglandin $E_2$ may be synthesized as described in Corey et al., *J. Am. Chem. Soc.,* vol 92, p. 397 (1970); Corey et al., *J. Am. Chem. Soc.,* vol. 92, p. 2586 (1970); and Heather et al., *Tetrahedron Letters,* p. 2313 (1973).

Both prostaglandin $E_1$ and $E_2$ are commercially available from Sigma Chemical Company of St. Louis, Mo.

By the term "15-hydroxyprostaglandindehydrogenase inhibitor" it is meant any compound which exhibits a significant and selective inhibition of prostaglandin degrading enzyme, or 15-hydroxyprostaglandindehydrogenase (PGDH). Two forms of 15-hydroxyprostaglandindehydrogenase (PGDH) are known: Type I, which is NAD+ dependent, and Type II, which is NADP+ dependent. Type I operates at a Km one order of magnitude lower than Type II and is thus more significant physiologically. Type I PGDH is described in Mak et al, *Biochimica et Biophysica Acta,* vol. 1035, pp. 190–196 (1990); Ensor et al, *J. Lipid Mediators Cell Signalling,* vol. 12, pp. 313–319 (1995); and Berry et al, *Biochemical Pharmacology.* vol. 32, no. 19, pp. 2863–2871 (1983), which are incorporated herein by reference. Partially purified bovine lung Type I PGDH is commercially available from BDH, Limited (Poole, UK). Berry et al., Tai et al., Muramatsu et al., and Mak et al. describe assays for determining enzymatic activity of Type I PGDH as well as methods for determining the degree of inhibition of this enzyme.

Type II PGDH is described in Chang, et al, *Biochem. Biophys. Res. Commun.,* vol. 99, pp. 745–751 (1981); Jarabak, et al, *Prostaglandins,* vol. 18, pp. 241–246 (1979), and Lin, et al, *Biochem. Biophys. Res. Commun.,* vol. 81, pp. 1227–1234 (1978), all of which are incorporated herein by reference.

Examples of suitable 15-hydroxyprostaglandinhdehydrogenase inhibitors include glycyrrhizic acid, licorice, glycyrrhetinic acid, various glycosides of glycrrhetinic acid, carboxenolone, DHEA, spironolactone, sofalcone, and sulphasalazine and analogues thereof. Antibodies which bind to and inhibit Type I PGDH may also be used.

Glycyrrhizic acid is also known as glycyrrhizin, glycyrrhizinic acid, and glycyrrhetinic acid glycoside. The formal chemical name is 20β-carboxy-11-oxo-30-norolean-12-en- 3β-yl-2-O-β-D-glucopyranuronosyl-α-D-glucopyranosiduronic acid, and the structure is:

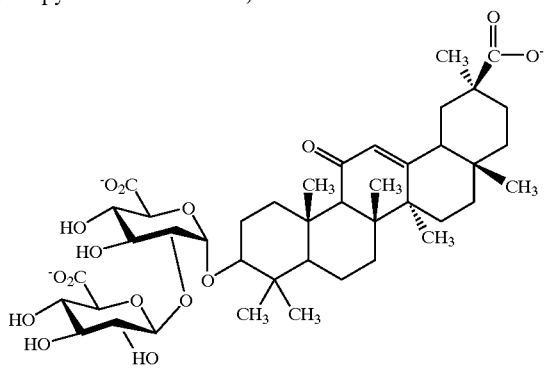

Glycyrrhizic acid is commercially available from Sigma Chemical Company of St. Louis, Mo.

Glycyrrhetinic acid is unglycosylated glycyrrhizic acid, and its structure is:

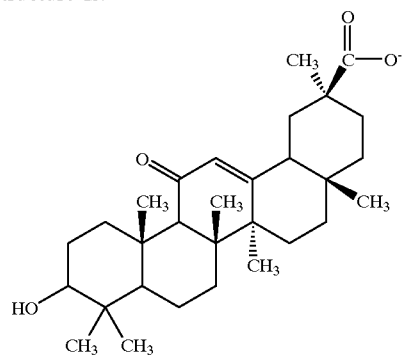

Glycyrrhetinic acid may be obtained from licorice extract.

Carbenoxolone is also known as 3β-hydroxy-11-oxo-20β-olean-12-en-29-oic acid hydrogen butanedioate and has the following structure:

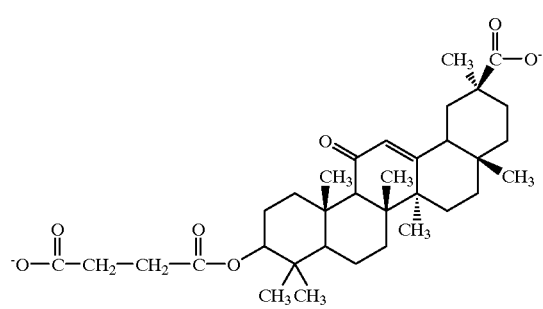

Carboxenolone may be synthesized as described in U.S. Pat. No. 3,070,623, which is incorporated herein by reference.

Licorice is also known as sweet root liquorice and glycyrrhiza and is described in the Merck Index, 10$^{th}$ edition, citation 4368 as "glycyrrhiza, Licorice, liquorice; sweet root. Dried rhizome and root of Glycyrrhiza glabra L., var. typica Regel & Herder (Spanish licorice), or of G. Glabra L., var. glandulifera (Waldst. & Kit.) Regel & Herder (Russian licorice), or of other varieties of G. g yielding a yellow and sweet wood, Leguminosaw. Habt. Southern Europe to Central Asia. Constit. 6–14% glycyrrhizin (the glucoside of glycyrrhetic acid), asparagine, sugars, resin."

Licorice is a crude preparation prepared from dried rhizomes or roots and as such contains large numbers of compounds many of which are not identified. A simple aqueous extract of a commercially available dried licorice root preparation may be prepared as follows. Two grams of this dried licorice root was mixed with 10 mls of distilled water, stirred until thoroughly mixed at room temperature and filtered to remove particulate matter. This simple aqueous extract of licorice is effective in inhibiting PGDE and may be used as is in the present invention.

Spironolactone is also known as Aldactone A or Verospiron. The formal chemical name of spironolactone is 17-hydroxy-7-mercapto-3-oxo-17α-pregn-4-ene-21-carboxylic and γ-lactone, 7-acetate, and the structure is:

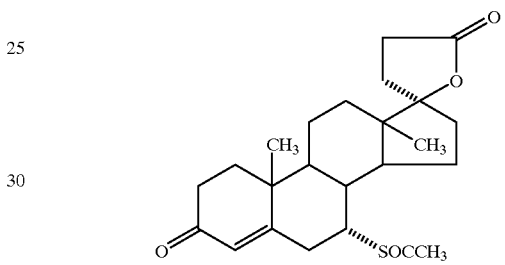

Spironolactone is commercially available from Sigma Chemical Company of St. Louis, Mo.

Sofalcone is formally known as [5-[(3-methyl-2-butenyl)oxy]-2-[3-[4[(3-methyl-2-butenyl)oxy]phenyl]-1-oxo-2-propenyl]phenoxy]acetic acid and has the formula:

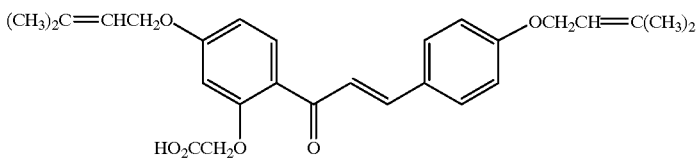

Sofalcone may be prepared as described in U.S. Pat. No. 4,085,135, which is incorporated herein by reference.

DHEA is formally known as 3-hydroxyandrost-5-en-17-one or dehydroepiandrosterone or prasterone. The structure of DHEA is:

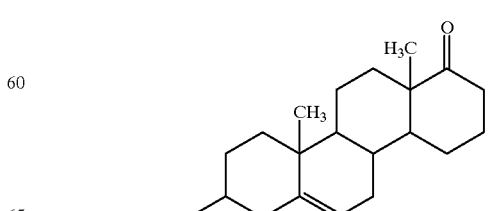

DHEA may be prepared as described in H. Hosoda et al, *J. Org. Chem.*, vol. 38, P. 4209 (1973), which is incorporated herein by reference.

Sulfasalazine is also known as 2-hydroxy-5[[4-[(2-pyridinylamino)sulfonyl]phneyl]azo]benzoic acid and has the structure:

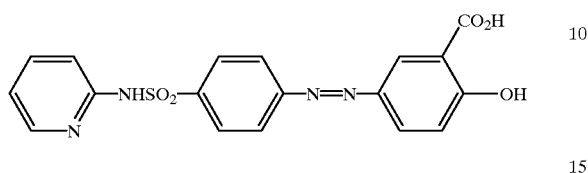

A number of sulfasalazine analogs have been shown to be inhibitors of PGDH by Berry et al, *Biochemical Pharmacology*, vol. 32, pp. 2863–2871 (1983). Examples of sulfasalazine analogs which may be used as the PGDH inhibitor in the present compositions include:

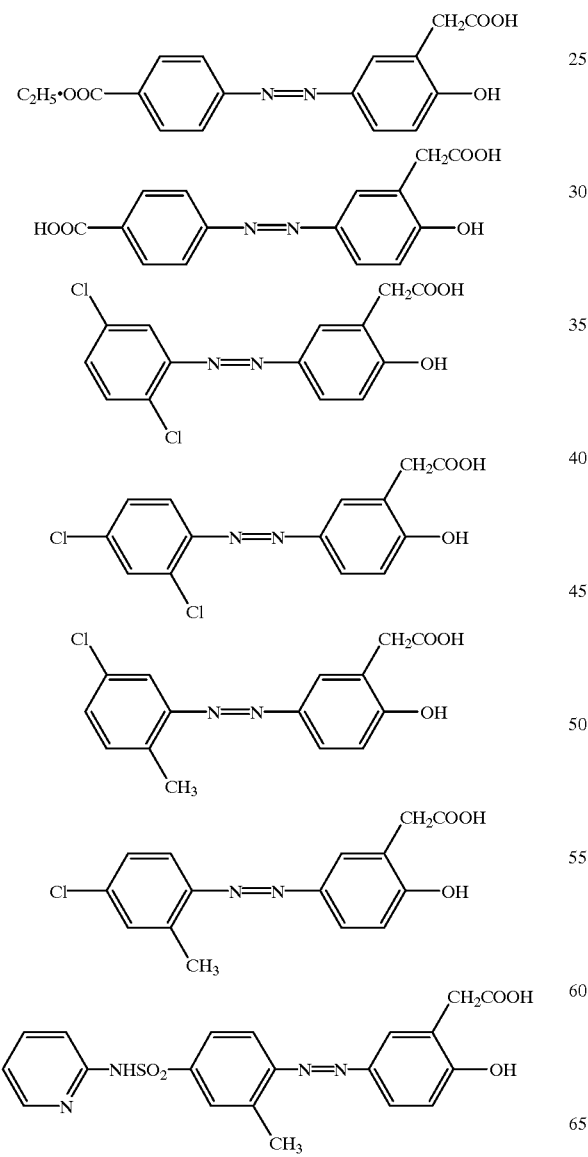

-continued

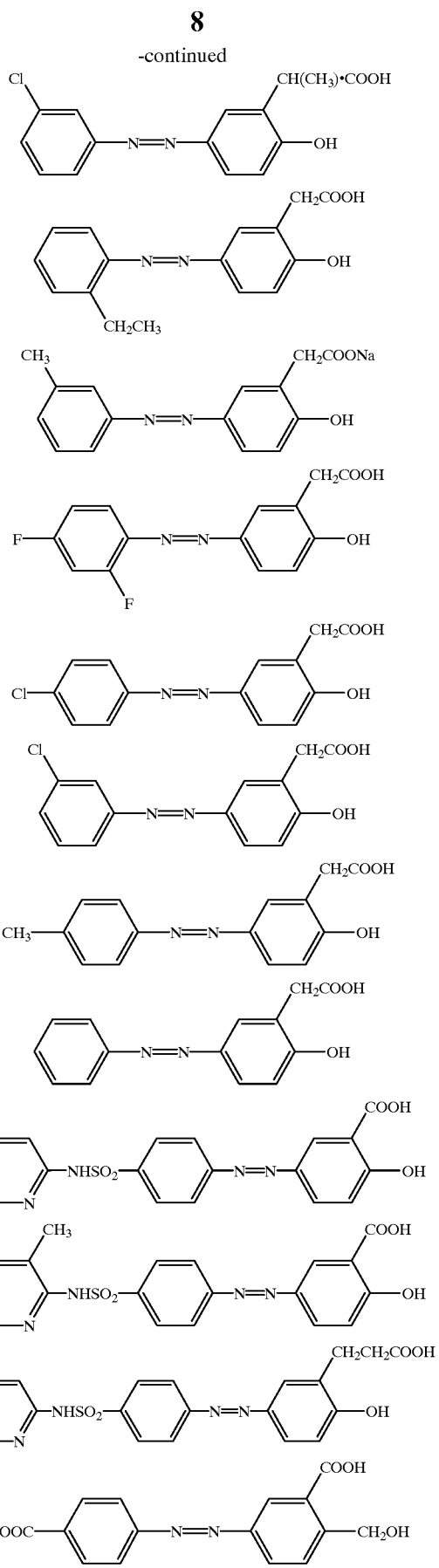

-continued

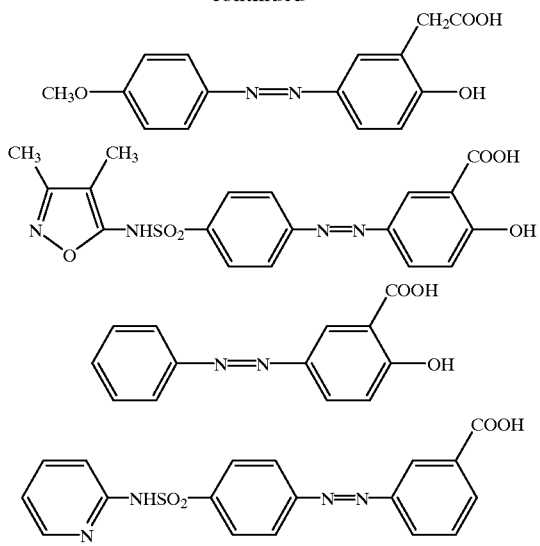

Typically, the present composition will contain prostaglandin $E_1$ or prostaglandin $E_2$ in an amount of 10 to 2,000 µg, preferably 20 to 500 µg per unit dosage.

The 15-hydroxyprostaglandindehydrogenase inhibitor will typically be present in an amount of 25 to 100, preferably 50 to 100, pig penile units of PGDH inhibition activity, per unit dosage. The amount of inhibitor which corresponds to a unit of pig penile PGDH inhibition activity is determined using either the spectrophotometric or radio-chemical assay described in the Examples. For inhibitors which exhibit a significant absorption at 340 nm, it is preferred to use the radio-chemical assay.

The present pharmaceutical compositions may take any form which is suitable for administration to the penis either via injection into the corpora cavernosa or transurethral administration, or topically applied to the urethral meatus. In the case of injection into the corpora cavernosa, the pharmaceutical composition is suitably in the form of a saline solution. Preferably, the pharmaceutical composition is in a form suitable for transurethral administration, and in this case the composition is typically in the form of a solution, an ointment, or a suppository.

Preferably, the pharmaceutical composition is in the form of a suppository. Typically, the suppository will comprise (a) either prostaglandin $E_1$, prostaglandin $E_2$, or a mixture thereof; and (b) a 15-hydroxyprostaglandindehydrogenase inhibitor; dispersed in a polyethylene glycol (PEG) matrix. The PEG is chosen so that the suppository is a solid or semisolid at room temperature but melts/dissolves rapidly in the urethra. Good results have been achieved using PEG with an average molecular weight of about 1450.

Typically, the suppository will contain sufficient amounts of (a) and (b) such that administration of a single suppository is sufficient to provide the desired result. Thus, a suppository would typically contain: (a) 0.01 to 2.0 mg, preferably 0.02 to 0.50 mg of prostaglandin $E_1$, or 0.01 to 2.0 mg, preferably 0.02 to 0.50 mg of prostaglandin $E_2$; and (b) 25 to 100 pig penile units, preferably 50 to 100 pig penile units, of the 15-hydroxyprostaglandindehydrogenase inhibitor.

The present pharmaceutical compositions may further comprise agents such as mast cell stabilizers (e.g., chromolyn and nedochromolyn), angiotensin converting enzyme (ACE) inhibitors (e.g., captopril, lisinopril, benazepril, enalapril, fosinopril sodium, quinapril, ramipril, and spirapril), zileuton, piripost, MK-886, MK-0591, ICI-D2318, docebenone, and leukotriene receptor antagonists.

The addition of ACE inhibitors such as captopril will decrease long term complications such as inflammatory and fibrotic responses.

Muscarinic agents such as pilocarpine, edrophonium, and bethanacol may also be added to increase the effectiveness of the compositions by stimulating the parasympathetic nervous system.

Agents which inhibit phosphodiesterase such as caffeine, aminophylline, sildenafil, theophylline, amrinone and milrinone may also be effective in enhancing the effectiveness of the mixture and prolonging the effect.

Kinin, kallekrin and leukotriene blockers will also decrease the burning associated with the administration of prostaglandins and help prevent fibrosis.

In a second embodiment, the present invention provides a method for treating male erectile dysfunction, by administering a pharmaceutical composition which comprises (a) prostaglandin $E_1$, prostaglandin $E_2$, or a mixture thereof; and (b) a 15-hydroxyprostaglandindehydrogenase inhibitor. The present method may be advantageously carried out using any of the present pharmaceutical compositions described above.

In the present method, the pharmaceutical composition may be administered either by topical administration to the urethral meatus or by injection into the corpora cavernosa or via transurethral administration. Injection into the corpora cavernosa may be carried out as described in Botto I. Linet and Frances G. Ogrinc, New England Journal of Medicine, vol. 334, pp. 873–877 (Apr. 4, 1996), which is incorporated herein by reference. Preferably, the present method involves topical or transurethral administration. Topical administration may be carried out by dripping a solution of the composition directly on the urethral meatus. Alternatively, a suppository may be placed directly into the urethral meatus. Transurethral administration may be carried out by application of a solution, ointment, emulsion, suppository, or any liquid form via a catheter as described in Herin Padam-Nathan et al., New England Journal of Medicine, vol. 336, pp. 1–7 (Jan. 2, 1997); and Wolfson V., et al., Urology, vol. 42, pp. 73–75 (1993), which are incorporated herein by reference. Preferably, the present method is carried out by topical administration of a suppository. Suppositories may be administered transurethrally using a device such as those described in Herin Padam-Nathan et al., New England Journal of Medicine, vol. 336, pp. 1–7 (Jan. 2, 1997), which is incorporated herein by reference.

Typically, the pharmaceutical composition is administered 1 to 50 minutes, preferably 10 to 20 minutes, prior to the time of commencing sexual intercourse. Suitably, the present method is carried out by administering one of the present pharmaceutical compositions described above. Preferably, the present method is carried out by either intraurethral administration of the present suppository or topical application of the present solution, cream, or ointment to the urethral meatus.

Of course, it is also to be understood that the prostaglandin $E_1$ or prostaglandin $E_2$ need not be administered simultaneously with the 15-hydroxyprostaglandindehydrogenase inhibitor. Rather, the 15-hydroxyprostaglandindehydrogenase inhibitor may be preadministered. Pre-treatment or simultaneous treatment with a 15-hydroxyprostaglandindehydrogenase inhibitor also decreases the burning sensation associated with the administration of the prostaglandin. In addition, the blocking of the PGDH enhances tremendously the absorption and effectiveness of the prostaglandin leading to a remarkably lower dose requirement.

Since PGDH degrades most pharmacologically active prostoglandins, not just $PGE_1$ and $PGE_2$, the inhibition of PGDH may be used in combination with any prostaglandin or prostaglandin analogue which is suitable for inclusion in the present compositions by nature of its vasodilating activity.

Other features of the invention will become apparent in the course of the following descriptions of exemplary embodiments which are given for illustration of the invention and are not intended to be limiting thereof.

EXAMPLES

I. PGDH Activity

A. Pig Penile Urethral Mucosa Preparation: Fresh hog penises from sexually mature animals are obtained from a local slaughter house. They are immediately washed in tap water and then in normal saline. The urethra corresponding to the section extending from the fossa navicularis and extending to the membraneous region of the urethra is separated from the corpus spongiosum. This region is called the penile urethra, and the corresponding length of the urethra is measured in millimeters and recorded. The weight of the urethra is also recorded. The mucosa is homogenized with four volumes of an ice-cold 100 mM potassium phosphate buffer (pH 7.5) containing 1 mM EDTA. Following centrifugation at 15,000 g for 15 minutes, the resultant supernatant fraction is used as the enzyme source of the penile mucosa.

B. 15-Hydroxyprostaglandindehydrogenase (PGDH) Activity Determination:

Spectrophotometric analysis:

As a substrate, prostaglandin $E_1$ is incubated with the pig penile urethral mucosa prepared above. The reaction mixture is contained in a total volume of 2.0 ml of the same buffer used above for the preparation of the pig penile urethral mucosa preparation.

Prostaglandin $E_1$ (50 microM) and NAD (300 microM) are used as substrates. The reaction is initiated by the addition of the prostaglandin $E_1$. Incubation is done at 37° C. and is terminated by the addition of 0.5 mL of 2NaOH. The oxidation of the prostaglandin is assayed by monitoring the reduction of NAD+ at 340 nanometers in a spectrophotometer. Reaction times are adjusted so that the initial quantity of prostaglandin is oxidized by 50 to 80%.

Radiochemical determination: The same reactions conditions listed for spectrophotometric analysis are used except that (5, 6, 8, 11, 12, 14, 15(n)-$^3$H)-prostaglandin $E_2$ (specific activity, 171 Ci, mmol) from Dupont de Nemours is used as a typical substrate. Any other tritiated prostaglandin substrate can be utilized in this assay. To terminate the reaction, methanol precipitation (75% volume/volume)) is performed; then, water is added to dilute the methanol to 10 volume percent. Soluble phase extractions are performed using octadecyl 18-C silica cartridges (J. T. Baker, Deventer, Holland. Dried extracts are run on 20×20, 60A silica plates using the organic phase of ethyl acetate/acetic acid/ isooctane/water (11:2:5:10:). Authentic prostaglandin $E_2$, 15-keto-prostaglandin $E_2$, and 13, 14-dihydro-15-keto-prostaglandin $E_2$ are comigrated on separate lanes. After localization of the compounds using phosphomolybdic spray, the silica is scraped, and the respective amounts of prostaglandin in $E_2$ and 15-keto-prostaglandin $E_2$ are determined by radioactive counting. A mU is defined as that amount of enzyme which oxidizes 1 n mole of prostaglandin $E_2$ per min at 37° C., pH 7.5. The number of mU PGDH per mm of pig penile urethra is then calculated by dividing the total number of mU by the mm of urethra used to prepare the enzyme.

II. PGDH Inhibitor Activity Determination

In the context of the present invention, one pig penile unit of PGDH inhibition activity is defined as the quantity of inhibitor that prevents one percent of the quantity of prostaglandin present from being oxidized, using the assay described below on a pig penile urethra of 5 mm.

Spectrophotometric: Using the above listed spectrophotometric analytical system for PGDH activity, the inhibitor in question is added to the reaction mixture prior to the addition of the prostaglandin $E_1$. At termination of the reaction, the quantity of the prostaglandin $E_1$ degraded is calculated and compared to the reaction without the inhibitor. Percent inhibition is defined as B/A×100 where
A=nmoles of prostaglandin oxidized without inhibitor.
B=nmoles prostaglandin oxidized with inhibitor.
For example, if A=50 nmoles and B=25 nmoles with inhibitor C, then inhibitor C gives 25/50×100 or 50% inhibition in this assay.

Radiochemical Determination: The assay for inhibition is run with and without inhibitor added as listed above in the determination of PGDH activity radiochemically. A given inhibitor is added to the reaction mixture just prior to the addition of the prostaglandin $E_1$ being analyzed and the analysis performed as listed. The quantity of prostaglandin oxidized is calculated and interpreted as listed above for spectrophotometric analysis of inhibitor activity.

Reference Example

An aqueous solution containing 250 μg of PGE2, and 150 μg of phentolamine hydrochloride was applied directly to the urethra of a 42 year old male with a history of erectile dysfunction. An erection was produced in 10 minutes. It lasted for 60 minutes.

Example 1

The urethra of a 42 year old male with a history of erectile dysfunction was pretreated with 1 ml of 0.9 percent (w/v) DHEA in water. After 15 minutes, an aqueous solution containing 250 μg of PGE 2 and 150 μg of phentolamine hydrochloride was applied directly to the urethra. An absence of burning was noted and an enhanced effectiveness was seen.

Example 2

An aqueous solution containing: 0.1 ml of 10% w/v carbenoxolone was applied topically to the urethral meatus of a 42 year old male with a history of erectile dysfunction for 5 minutes before application of 500 μg of PGE2 and 500 μg of phentolamine, in liposomes. An erection was produced in 15 minutes and lasted for 90 minutes.

Example 3

A 47-year-old white male without history of erectile dysfunction was evaluated for cavernosal arterial blood flow using a KNOLL/MIDUS system by Urometrics, Inc. ultrasonic doppler flow analyzer. The baseline for unstimulated blood flow in the penile cavernosal arteries was 0.025 meters/second (see FIG. 1). A #12 French catheter was inserted into the urethra 4 centimeters and 150 nanomoles of carbenoxolone (PGDH inhibitor) was infused as a pretreatment 15 minutes prior to infusion of 150 nanomoles of $PGE_2$ and phentolamine hydrochloride (a 1:1 molar ratio of enzyme inhibitor to prostaglandin). Cavernosal artery blood flow increased over the next 15 minutes to 0.45 meters per second which is an 18-fold increase in cavernosa blood flow (see FIG. 1).

Ten to one molar ratio of inhibitor to $PGE_2$ gave a cavernosal blood flow of 0.72 meters per second at 15 minutes which is a 29-fold increase in cavernosal arterial blood flow.

Example 4

A 46-year-old white male with a history of intermittent erectile difficulties was assessed for baseline cavernosal arterial blood flow using the KNOLL/MIDUS system; baseline (flaccid) blood flow was undetectable. 150 nanomoles of carbenoxolone were used as a pretreatment followed by 150 nanomoles of $PGE_2$ and phentolamine as in Example 3. After 15 minutes, cavernosal blood flow was 0.3 meters per second which is at least a 12-fold increase of blood flow to the penis. Administration of a 10 to 1 molar ratio of inhibitor to $PGE_2$ resulted in 0.35 meters per second cavernosal arterial blood flow at 15 minutes which is at least a 14-fold increase blood flow. (See FIG. 1).

Example 5

A 42-year-old white male with a history of erectile dysfunction was assessed using the KNOLL/MIDUS system; baseline blood flow (flaccid) was 0.03 meters per second. Using a #12 French catheter placed 4 centimeters into the urethra, 3.0 micromoles of carbenoxolone were used as a pretreatment to inhibit prostaglandin degradation. Then, 0.75 micromoles of $PGE_2$ and phentolamine hydrochloride were administered intraurethrally (which is a 4 to 1 molar ratio of inhibitor to $PGE_2$). After 15 minutes, cavernosal blood flow had increased to 0.49 meters per second which is a 16.3-fold increase in cavernosal arterial blood flow (see FIG. 1).

Example 6

Using the KNOLL/MIDUS system, the basal (flaccid) cavernosal arterial blood flow on a 42-year-old white male with erectile dysfunction was found to be 0.03 meters/second. 6.6 micromoles of carbenoxolone in a suppository of polyethyleneglycol MW 1450 was placed on the urethral meatus and allowed to dissolve for 15 minutes prior to administration of 0.83 micromoles of $PGE_2$ and phentolamine (an 8 to 1 molar ratio of inhibitor to $PGE_2$). Cavernosal arterial blood flow increased over the next 15 minutes 0.43 meters per second which is a 14-fold increase in blood flow (see FIG. 1).

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for treating male erectile dysfunction, comprising administering to a patient in need thereof an effective amount of (a) a vasodilator; and (b) a 15-hydroxyprostaglandindehydrogenase enzyme inhibitor.

2. The method of claim 1, wherein said vasodilator is prostaglandin $E_1$.

3. The method of claim 1, wherein said vasodilator is prostaglandin $E_2$.

4. The method of claim 1 wherein said 15-hydroxyprostaglandindehydrogenase inhibitor is selected from the group consisting of glycyrrhizic acid, licorice, DHEA, spironolactone, and sofalcone.

5. The method of claim 1, wherein said (a) and (b) are comprised in a pharmaceutical composition which is in a form selected from the group consisting of solutions, ointments, and suppositories.

6. The method of claim 1, wherein said (a) and (b) are comprised in a pharmaceutical composition which is in the form of a suppository.

7. The method of claim 1, wherein said pharmaceutical composition is administered either via injection into said patient's corpora cavernosa or transurethrally.

8. The method of claim 1, wherein said pharmaceutical composition is administered transurethrally.

9. The method of claim 1, wherein said pharmaceutical composition is administered topically to the urethral meatus.

10. The method of claim 2, which comprises administering 0.01 to 2.0 mg of said prostaglandin $E_1$ and 25 to 100 units of said 15-hydroxyprostaglandindehydrogenase inhibitor.

11. The method of claim 3, which comprises administering 0.01 to 2.0 mg of said prostaglandin $E_2$ and 50 to 100 units of said 15-hydroxyprostaglandindehydrogenase inhibitor.

12. The method of claim 2, which comprises administering 20 to 500 μg of said prostaglandin $E_1$.

13. The method of claim 2, which comprises administering 20 to 500 μg of said prostaglandin $E_1$ and 25 to 100 units of said 15-hydroxyprostaglandindehydrogenase inhibitor.

14. The method of claim 2, which comprises administering 20 to 250 μg of said prostaglandin $E_1$.

15. The method of claim 2, which comprises administering 20 to 250 μg of said prostaglandin $E_1$ and 25 to 100 units of said 15-hydroxyprostaglandindehydrogenase inhibitor.

16. The method of claim 3, which comprises administering 20 to 500 μg of said prostaglandin $E_2$.

17. The method of claim 3, which comprises administering 20 to 500 μg of said prostaglandin $E_2$ and 25 to 100 units of said 15-hydroxyprostaglandindehydrogenase inhibitor.

18. The method of claim 3, which comprises administering 20 to 250 μg of said prostaglandin $E_2$.

19. The method of claim 3, which comprises administering 20 to 250 μg of said prostaglandin $E_2$ and 25 to 100 units of said 15-hydroxyprostaglandindehydrogenase inhibitor.

* * * * *